US012700519B2

(12) United States Patent
Chudakov et al.

(10) Patent No.: US 12,700,519 B2
(45) Date of Patent: Aug. 4, 2026

(54) METHOD FOR MANUFACTURING AND INCREASING THE YIELD OF A MEDICAL STRONTIUM-82/RUBIDIUM-82 GENERATOR

(71) Applicant: NAOGEN PHARMA, Saint-Herblain (FR)

(72) Inventors: Valery Mikhailovich Chudakov, Moscow (RU); Sergey Vasilievich Shatik, Saint-Petersburg (RU); Boris Leonidovich Zhuikov, Moscow (RU)

(73) Assignee: NAOGEN PHARMA, Saint-Herblain (FR)

( * ) Notice: Subject to any disclaimer, the term of this patent is extended or adjusted under 35 U.S.C. 154(b) by 502 days.

(21) Appl. No.: 18/553,508

(22) PCT Filed: May 25, 2022

(86) PCT No.: PCT/RU2022/000176

§ 371 (c)(1),
(2) Date: Sep. 29, 2023

(87) PCT Pub. No.: WO2022/211675

PCT Pub. Date: Oct. 6, 2022

(65) Prior Publication Data

US 2024/0194366 A1 Jun. 13, 2024

(51) Int. Cl.
| | |
|---|---|
| *G21G 4/08* | (2006.01) |
| *A61K 51/12* | (2006.01) |
| *B01D 15/08* | (2006.01) |
| *B01J 20/06* | (2006.01) |

(Continued)

(52) U.S. Cl.
CPC ............. *G21G 4/08* (2013.01); *A61K 51/121* (2013.01); *B01D 15/08* (2013.01); *B01J 20/06* (2013.01);

(Continued)

(58) Field of Classification Search
CPC .. G21G 4/08; G21G 1/04; B01J 20/282; B01J 20/3092; B01J 2220/52; A61K 51/121
See application file for complete search history.

(56) References Cited

U.S. PATENT DOCUMENTS

2015/0260855 A1* 9/2015 McQuaid ................ G01T 1/161
422/69

FOREIGN PATENT DOCUMENTS

| | | |
|---|---|---|
| RU | 2507618 C2 | 2/2014 |
| RU | 2538398 C1 | 1/2015 |

(Continued)

OTHER PUBLICATIONS

International Search Report for PCT/RU2022/000176 mailed Oct. 6, 2022, 2 pages.

(Continued)

*Primary Examiner* — David E Smith
(74) *Attorney, Agent, or Firm* — NIXON & VANDERHYE

(57) ABSTRACT

Disclosed is a method for preparing a strontium-82/rubidium-82 generator. The method includes: filling a column volume with a sorbent made of hydrated tin (IV) oxide; passing through the column an initial solution with strontium-82 radionuclide, which also contains ions of stable isotopes of calcium and strontium; and washing out rubidium-82 with a saline solution of 0.9% sodium chloride. In order to achieve a breakthrough of strontium-82 or strontium-85 below permissible levels, 0.01 and 0.1 kBq per 1 MBq $^{82}$Rb, respectively, when passing not less than 17 liters of saline solution through columns with a volume of not less than 1.6 cm$^3$ and a dry sorbent weight of not less than 3.8 g, a specific activity of strontium-82 in the initial (Continued)

solution is not less than 90 GBq (2400 mCi) per mg of stable strontium cations for a generator with an activity of 3700 MBq (100 mCi).

6 Claims, 5 Drawing Sheets

(51) Int. Cl.
B01J 20/282 (2006.01)
B01J 20/30 (2006.01)
G21G 1/04 (2006.01)

(52) U.S. Cl.
CPC ......... B01J 20/282 (2013.01); B01J 20/3092 (2013.01); G21G 1/04 (2013.01); B01J 2220/52 (2013.01)

(56) References Cited

FOREIGN PATENT DOCUMENTS

| | | | |
|---|---|---|---|
| RU | 2546731 C1 | 4/2015 | |
| WO | 2006135374 A2 | 12/2006 | |
| WO | 2010020596 A1 | 2/2010 | |
| WO | WO-2019191386 A1 * | 10/2019 | ........... G21G 1/0005 |

OTHER PUBLICATIONS

Written Opinion of the ISA for PCT/RU2022/000176 mailed Oct. 6, 2022, 4 pages.

* cited by examiner

METHOD FOR MANUFACTURING AND INCREASING THE YIELD OF A MEDICAL STRONTIUM-82/RUBIDIUM-82 GENERATOR

CROSS-REFERENCE TO RELATED APPLICATIONS

This application is the U.S. national phase of International Application No. PCT/RU2022/000176 filed May 25, 2022 which designated the U.S. and claims priority to RU 2021108460 filed Mar. 30, 2021, the entire contents of each of which are hereby incorporated by reference.

FIELD OF THE INVENTION

The present invention relates to products for nuclear medicine, namely, to radioisotope generators of the sorption type, the principle of operation of which is based on the elution of a short-lived "daughter" radionuclide formed as a result of radioactive decay of a relatively long-lived "parent" radionuclide.

BACKGROUND ART

From the existing art, various radionuclide generators for medical purposes and methods for their preparation are known [Radionuclide Generators. New Systems for Nuclear Medicine Applications. Knapp, F. et al. ASC Symposium Series; American Chemical Society: Washington, DC, 1984].

The strontium-82/rubidium-82 generator is intended to multiple generation of sterile and apirogenic radiopharmaceuticals with $^{82}$Rb. It includes a generator column with a sorbent based on hydrated tin (IV) oxide, which is loaded with the radioactive isotope $^{82}$Sr (half-life 25.55 days) with an activity from 1800 to 5920 MBq [V. M. Chudakov et al. Investigation of the characteristics of the $^{82}$Rb generator for positron emission tomography. Radiochemistry, vol. 56, pp. 535-543, 2014] decaying into rubidium-82 (half-life of 76 s). The generator column in a metallic case is inserted into a container made of tungsten or lead, which protects from ionizing radiation. Radiopharmaceutical obtained from the generator and directly injected into the patient usually has rubidium-82 activity from 700 to 2500 MBq [V. M. Chudakov et al. Investigation of the characteristics of the $^{82}$Rb generator for positron emission tomography. Radiochemistry, vol. 56, pp. 535-543, 2014] and may contain impurities of strontium-82 no more than 0.01 kBq per 1 MBq of rubidium-82, as well as concomitant radioactive strontium-85 no more than 0.1 kBq per 1 MBq of rubidium-82 [CARDIOGEN-82® Rb 82 Generator. Expiration Data. Manufactured for Bracco Diagnostics Inc., Monroe Twp., NJ 08831by GE Healthcare, Medi-Physics, Inc., South Plainfield, NJ 07080, 46-8200D, NDC: 0270-0091-01, 2014], [CardioGen-82: Package Insert and Label Information. https://druginserts.com/lib/rx/meds/cardiogen-82-1/].

The generator yield is determined by the volume of radiopharmaceutical solution, which can be obtained from the generator before strontium breakthrough (appearance of unacceptable quantity of strontium radionuclides). The occurrence of a strontium breakthrough during the operation of the generator is defined as reaching the maximum limit value of the ratio of 0.01 kBq $^{82}$Sg/1 MBq $^{82}$Rb or 0.1 kBq $^{85}$Sr/1 MBq $^{82}$Rb for any portion of the radiopharmaceutical solution. The total volume of the obtained eluate corresponding to this value is defined as the Expiration Limit and is from 17 I [CardioGen-82: Package Insert and Label Information. https://druginserts.com/lib/rx/meds/cardiogen-82-1/] up to 30 I [V. M. Chudakov et al. Investigation of the characteristics of the $^{82}$Rb generator for positron emission tomography. Radiochemistry, vol. 56, pp. 435-543, 2014], [N. A. Kostennikov et al. $^{82}$Sr/$^{82}$Rb generator and prospects for its application in neuro-oncology. Radiation therapy and diagnostics. No. 3(8), 2017, p. 5-13], [RUBY-FILL® (Rubidium Rb-82 Generators) and Elution System. https://dragsimage.com/products/USA/ruby-fill-(rubidium-rb-82-generator)-and-elution-system].

The resulting radiopharmaceutical is used in diagnostic procedures by positron emission tomography (PET) as a source of labeled $^{82}$Rb atoms in the study of myocardial perfusion (cardiology, blood flow), as well as to determine the integrity of the blood-brain barrier (neuro-oncology) and to visualize neoplasms in the brain and other organs of the human body. The total volume of eluate obtained at this point is one of the most important characteristics of the strontium-82/rubidium-82 generator and is related to the ionic capacity of the sorbent used in its production: the larger the ionic capacity of the sorbent in the generator, the larger the total volume of eluate (radiopharmaceutical) that meets the necessary characteristics.

The disadvantage of the known methods of preparing the generator is that the generators are prepared and loaded with strontium-82 using solutions where the concentration of divalent metal ions is accepted to be quite high. Despite the fact that in reality the specific activity of $^{82}$Sr in the solutions used can be higher than the minimal required value (925 MBq/mg, i.e., 25 mCi/mg) and amounts to hundreds of GBq/mg (several thousand mCi/mg), the calcium content in them is not strictly regulated. As a result, the volume of eluate up to the limit value of the strontium breakthrough in the generators is not stable and varies widely.

It is known that the maximum volume of the conditioned solution of RPh with rubidium-82 obtained with a generator is not a stable characteristic even for generators with the same columns, which was previously not completely clear [M. R. Cackette, T. J. Ruth, J. S. Vincent. 1993. $^{82}$Sr production from metallic Rb targets and development of $^{82}$Rb generator system. Appl. Radiat. Isot. 44: 917-922]. Due to the instability of the maximum volume of radiopharmaceutical before the strontium breakthrough, an undesirable unintended entry of strontium-82 and concomitant strontium-85 cations into the patient's body during a medical examination may occur. To prevent the entry of an inadmissible amount of radioactive strontium into the patient's body, the above-mentioned restriction—the Expiration limit—on the content of strontium in the eluate is established, at which the use of the generator stops. For CardioGen® generators manufactured by Bracco, an additional restriction has been set: even if the above parameters are not exceeded, but 17 I of conditioned eluate has been already received from the generator or the generator has been operated for 42 days, the use of the generator also stops. In addition, the quality control of the eluate from the generator is strengthened either after reaching the Alert Limit, which occurs when the content of strontium-82 and strontium-85 radionuclides in the RPh reaches the values of 0.002 kBq $^{82}$Sr/1 MBq $^{82}$Rb and 0.02 kBq $^{85}$Sr/1 MBq $^{82}$Rb, respectively, or when 14 I of conditioned eluate are obtained [CardioGen-82: Package Insert and Label Information. https://druginserts.com/lib/rx/meds/cardiogen-82-1/].

In accordance with the requirements, the $^{82}$SrCl$_2$ solution used for manufacture of the generator must have a volume activity of ≥1850 MBq/ml (≥50 mCi/ml) and a specific activity of ≥925 MBq/mg (>25 mCi/mg) [Strontium-82

Radiochemical Strontium Chloride Solution. Sr-82 Fact Sheet. MDS Nordion. Canada. NM01 10. Can. Rev. 05|04], [Strontium-82 product information. Product Catalog. Isotope Program. U.S. Department of Energy. National Isotope, Development Center. ORNL, 1996-2013]). At the minimum values of these characteristics of 1850 MBq/ml and 925 MBq/mg (50 mCi/ml and 25 mCi/mg), the total concentration of strontium cations in the solution is 2 mg/ml or about 23 $\mu$mol/ml, and the strontium content in the generator column with a dry sorbent weight of 3.8 g and strontium-82 activity of 3.7 GBq (100 mCi) is ~12 $\mu$mol/g. Often, solutions have a much higher specific activity. However, a higher specific activity is not a strict requirement, which leads to an unexpected unintentional enter of an unacceptable quantity of strontium-82 and strontium-85 into the patient's body, or an unexpected termination of the generator use.

As a result, the volume of the conditioned solution that can be obtained from such generators is limited to 10-17 liters of RPh.

The closest technical solution is also the method of preparing the strontium-82/rubidium-82 generator [Zhuikov B. L., Chudakov V. M., Kohanyuk V. M. Rubidium-82 generator and method of its preparation. RF patent 2546731, prior. 23.12.2013].

The disadvantage of this technical solution is that the concentration limits of the content of stable strontium and calcium ions in all solutions used for the preparation of the generator are not strictly regulated. As a result, the maximum volume of the obtained solution of radiopharmaceutical before the breakthrough of radioactive strontium is not stable, which leads to the strontium-82 breakthrough and undesirable incidents [NRC Information Notice 2019011: Strontium/Rubidium-82 generator elution Events and Issues. US Nuclear Regulatory Commission Office of Nuclear Material Safety and Safeguards, Washington, DC 20555, Dec. 23, 2019 https://www.nrc.gov/docs/ML1928/ML19281A220.pdf].

SUMMARY OF THE INVENTION

The technical result of the present invention is an increase in the volume of obtained radiopharmaceutical, which increases the yield of the generator, as well as a reduction in the risk of strontium breakthrough in a larger volume compared to known examples (prototype), which reduces the risk of radioactive strontium entering the patient's body.

The technical result is achieved by means of using solutions with a low and controlled content of stable strontium and calcium impurities during the process of preparing a generator.

The quality of the strontium-82/rubidium-82 generator depends, in particular, on the content of impurities in the $^{82}SrCl_2$ solution, since the sorption centers on the sorbent can be saturated with strontium and calcium ions. According to the data on the composition of impurities in the solution of strontium-82 chloride, the main inactive impurities which can compete with the absorption of $^{82}Sr^{2+}$ and $^{85}Sr^{+2}$, are divalent cations of alkaline-earth metals. Moreover, the amount of $Ca^{2+}$ is usually not less than 70-75% of all divalent cations, and the total amount of $Ca^{2+}$ and $Sr^{2+}$ is usually not less than 90-95%. In addition to $Ca^{2+}$ and $Sr^{2+}$, other divalent metal cations (mainly $Mg^{2+}$ and $Ba^{2+}$) may also be present in the strontium-82 chloride solution, which may also affect the quality of the prepared generator column. However, their content in the initial solutions is significantly less than that of calcium and strontium, and therefore, they should not have such a significant impact on the quality of the generator column and the value of the total volume of radiopharmaceutical of acceptable quality obtained from the generator.

The volume of eluate from the strontium-82/rubidium-82 generator, obtained before the breakthrough of $^{82}Sr^{2+}$ and $^{85}Sr^{+2}$ isotopes, greatly depends on the ionic capacity of the sorbent. The ionic capacity of the sorbent is determined by the number of metal ion sorption centers in it, which is proportional to the weight of the sorbent in the generator column. This characteristic also depends on the method of preparation of the sorbent base. It is reduced due to the sorption of impurity of competing stable metal ions, especially $Ca^{2+}$ and $Sr^{2+}$, which adsorbs onto the sorbent during its preparation, during the loading of the generator with radioactive strontium, as well as during the elution of rubidium-82 in solution (eluate) during operation of the generator. During operation of the generator, the total volume of eluate of radiopharmaceutical will be the higher, the lower the content of calcium cations and other alkaline earth metals in the eluent (the concentration of calcium cations in the eluent can reach up to 20 mg/l in some cases).

The object of the invention is to suggest a method for preparing a strontium-82/rubidium-82 generator, which, unlike the known ones, provides a maximal volume of the produced radiopharmaceutical solution of more than 30 liters, and minimizes the possibility of strontium breakthrough with smaller volumes of eluent. This object is achieved by the method of preparing the strontium-82/rubidium-82 generator that uses solutions with a certain content of strontium and calcium cations at a given radioactivity of the generator, in particular, a $^{82}SrCl_2$ solution with a specific activity of at least about one hundred GBq/mg (several thousand mCi/mg) is used, and when using $^{82}SrCl_2$ solutions with a lower specific activity, the object of the invention is achieved only with a larger weight of the sorbent in the generator column. The higher the activity of strontium-82 in the manufactured generator and the larger the volume of eluate of radiopharmaceutical to be obtained therefrom, the higher the specific activity of the $^{82}SrCl_2$ solution should be. At the same time, the total content of the main inactive impurities (strontium and calcium cations) on the sorbent of the generator column calculated as (1 $\mu$mol of strontium ions+0.11 $\mu$mol of calcium cations per g of dry sorbent) should be lower.

Thus, when using generators with a dry sorbent weight of at least 3.8 g to obtain not less than 17 liters of radiopharmaceutical solution from a generator with strontium-82 activity of 1.1 GBq (30 mCi) and 3.7 GBq (100 mCi), the specific activity of the $^{82}SrCl_2$ solution should be not less than 27 GBq (720 mCi) and 90 GBq (2400 mCi) per mg of stable strontium cations, respectively. While the content of strontium and calcium cations should be such that (1 $\mu$mol of strontium ions+0.11 $\mu$mol of calcium cations) per 1 g of dry sorbent it should be not more than 2.2 $\mu$mol and 0.67 $\mu$mol per 1 g of dry sorbent respectively.

To obtain not less than 30 liters of RPh from generators with a dry sorbent weight not less than 3.8 g and strontium-82 activity of 1.1 GBq (30 mCi) and 3.7 GBq (100 mCi), the specific activity of the $^{82}SrCl_2$ solution should be not less than 55 GBq (1450 mCi) and 180 GBq (4800 mCi) per mg of stable strontium cations, respectively. In this case, the content of strontium and calcium cations should be such that (1 $\mu$mol of strontium ions+0.11 $\mu$mol of calcium cations) per 1 g of dry sorbent it is no more than 1.10 $\mu$mol and 0.33 $\mu$mol per g of dry sorbent, respectively.

To obtain not less than 60 liters of RPh from a generator with a dry sorbent weight of not less than 3.8 g and strontium-82 activity of 1.1 GBq (30 mCi) and 3.7 GBq (100 mCi), the specific activity of the $^{82}SrCl_2$ solution should be not less than 90 GBq (2400 mCi) and 290 GBq (7900 mCi) per mg of stable strontium cations, respectively. In this case, the content of strontium and calcium cations should be such that (1 μmol of strontium ions+0.11 μmol of calcium cations) per 1 g of dry sorbent it is not more than 0.73 μmol and 0.22 μmol per g of dry sorbent, respectively.

Figure 1:
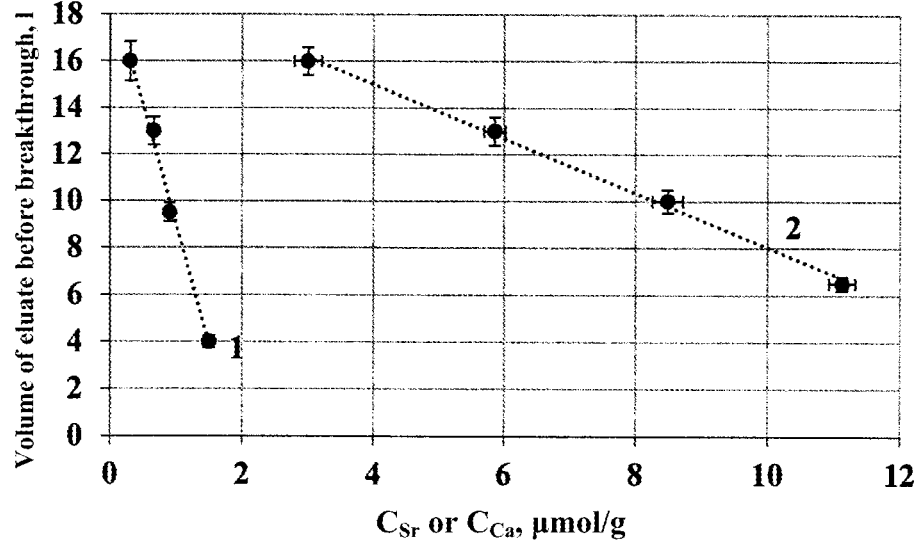
FIG. 1 shows the dependence of the total volume of eluate from the strontium-82/rubidium-82 generator before the strontium-82 breakthrough, where: 1—dependence on the $Sr^{2+}$ content in the generator column per 1 g of dry sorbent $C_{Sr}$ ($Ca^{2+}$ content ($C_{Ca}$=3.0 μmol/g in all columns); 2—dependence on $C_{Ca}$ ($C_{Sr}$=0.3 μmol/g in all columns). The volume of the columns is 1.6 cm³, the weight of the dry sorbent is 3.8 g.

The effect of the content of inactive calcium and strontium cations on the breakthrough is different. The result of the effect of the content of inactive strontium cations on the volume of the eluate before the strontium-82 breakthrough at a constant calcium content in the sorbent is shown in FIG. 1 (line 1). The result of the effect of the content of inactive calcium cations on the volume of the eluate before the strontium-82 breakthrough at a constant strontium content in the sorbent is shown in FIG. 1 (line 2). The ratio of the effectiveness of the effect of calcium and strontium is demonstrated in Example 1 and is 0.11.

Figure 2:
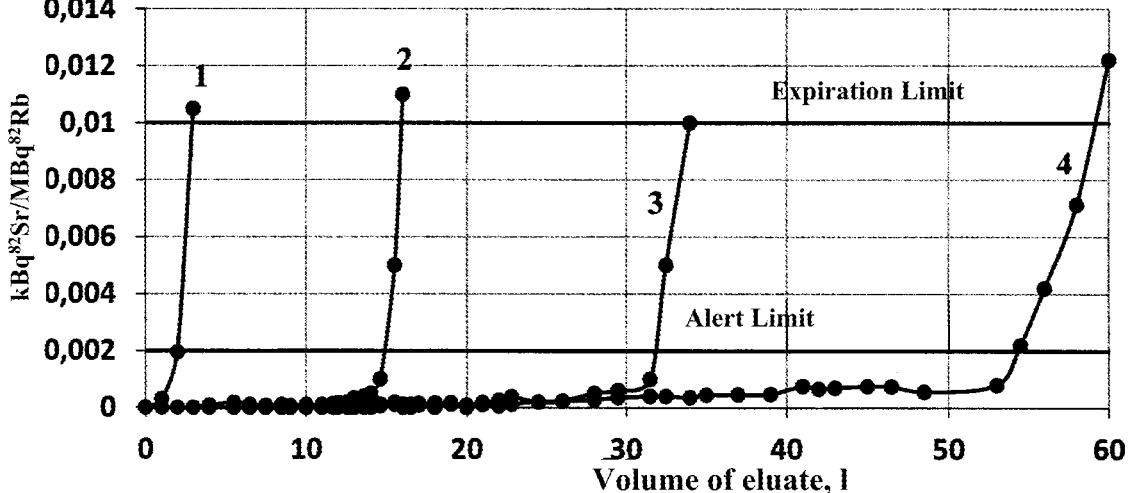
FIG. 2 shows the dependence of the ratio of $^{82}Sr$ activity to $^{82}Rb$ activity in the eluate from strontium-82/rubidium-82 generators with different volume of the generator column and the weight of the dry sorbent on the volume of the passed solution: 1—the volume of the generator column is 0.34 cm³ (weight 0.8 g; $C_{Ca}$=14.3 μmol/g; $C_{Sr}$=1.4 μmol/g); 2—the volume of the generator column is 1.6 cm³ (weight 3.8 g; $C_{Ca}$=3.0 μmol/g; $C_{Sr}$=0.3 μmol/g); 3—the volume of the generator column 3.0 cm³ (weight 7.2 g; $C_{Ca}$=1.6 mmol/g; $C_{Sr}$=0.16 μmol/g); 4—the volume of the generator column 5.0 cm³ (weight 12 g; $C_{Ca}$=1.0 μmol/g; $C_{Sr}$=0.1 μmol/g). Internal diameter and height of the generator column: 1-0.4 cm and 2.7 cm; 2-0.85 cm and 2.7 cm; 3-0.85 cm and 5.4 cm; 4-1.2 cm and 4.8 cm.

In Example 2, Table. 2 and FIG. 2 the effect of inactive impurities on the volume of eluate is demonstrated. Both the volume of eluate before reaching the Expiration Limit and the volume of eluate before reaching the Alert Limit are given. According to the existing regulations, when the Alert Limit is achieved, control over the content of strontium isotopes in the eluate is strengthened.

DETAILED DESCRIPTION OF THE EMBODIMENTS

Methods for preparing a rubidium-82 generator with the claimed characteristics are confirmed by the following examples.

Example 1

The preparation of strontium-82/rubidium-82 generators with generator columns of the same volume is carried out in accordance with the procedure in [Zhuikov B. L., Chudakov V. M., Kohanyuk V. M. Rubidium-82 generator and method of its preparation. RU 2 546 732 CU, priority date—23 Dec. 2013]. The prepared columns are: 1) with different content of calcium cations $C_{Ca}$ and the same content of strontium cations $C_{Sr}$ on the sorbent; 2) with different content of strontium cations $C_{Sr}$ and the same content of calcium cations $C_{Ca}$ on the sorbent.

The content of strontium-82 in the eluate is measured depending on the volume of the passed eluent before the breakthrough of the strontium isotopes (V). The results are shown in Table 1 and FIG. 1.

Table 1. Effect of the content of calcium cations $C_{Ca}$ or strontium cations $C_{Sr}$ on the sorbent in the generator column on the total volume of the obtained eluate before the strontium-82 breakthrough (V)

| $C_{Ca}$, μmol/g | $C_{Sr}$, μmol/g | V, I |
|---|---|---|
| 3.0 | 0.30 | 16 |
| 5.9 | 0.30 | 13 |
| 8.5 | 0.30 | 10 |
| 11.1 | 0.30 | 7 |
| 3.0 | 0.30 | 16 |
| 3.0 | 0.66 | 13 |
| 3.0 | 0.90 | 10 |
| 3.0 | 1.50 | 4 |

The example illustrates the different effects of strontium and calcium cations on the total eluate volume before the strontium-82 isotope breakthrough.

The total volume of eluate before the strontium-82 breakthrough decreases with an increase of the content of both calcium cations and strontium cations on the sorbent in the generator column. In both cases, the volume of eluate before the breakthrough of strontium-82 depends linearly on concentrations $C_{Ca}$ and $C_{Sr}$ according the equation V=a·C+b (where C is the concentration of calcium or strontium on the sorbent), and by the least squares method the values of parameters a and b can be determined. For calcium: a=−1.11 I·g/μmol, b=19.3 I ($r^2$=0.9996); and for strontium a=−10.14 I·g/mol, b=19.3 I ($r^2$=0.9984). Extrapolation of the linear dependence gives approximately 19 liters corresponding to a breakthrough at the strontium concentration on the sorbent $C_{Sr}$=0.3 μmol/g without calcium, or at $C_{Sr}$=3.0 μmol/g without strontium. The effect of changes in the concentration of calcium on the volume before the breakthrough is 0.11 in mol units versus the effect of changes in the concentration of strontium. Based on this, the volume before the breakthrough (V) depends on the value of $0.11 \cdot C_{Ca} + C_{Sr}$ (μmol/g).

Example 2

The preparation of strontium-82/rubidium-82 generators with generator columns of different volumes with different sorbent weights is carried out as described in Example 1. The content of the strontium-82 isotope in the eluate is measured versus the volume of the eluent. The results are shown in Table. 2 and are illustrated also in FIG. 2. The values of $C_{Ca}$ and $C_{Sr}$ and their total amount on the sorbent are given in the description to FIGS. 3 and 4.

Figure 3:
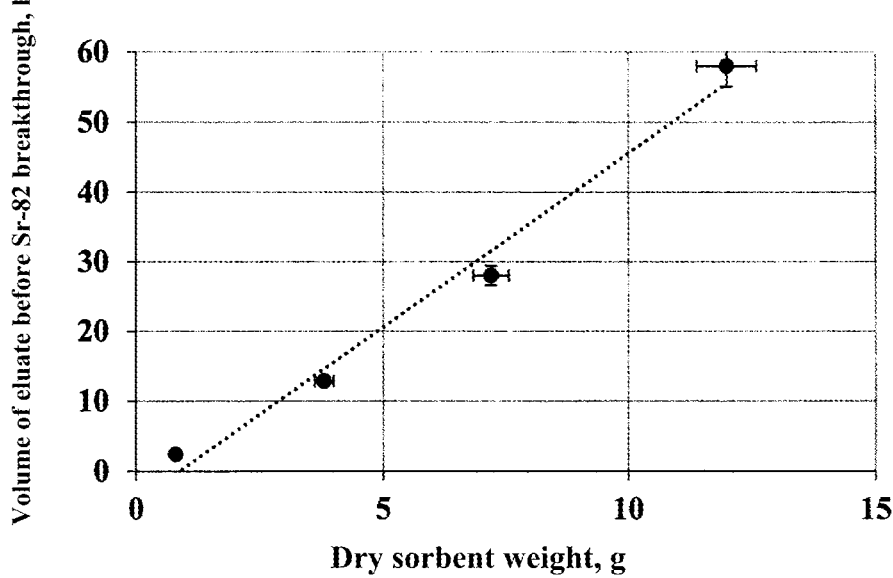
FIG. 3 shows the dependence of the total volume of eluate from the strontium-82/rubidium-82 generator before reaching the expiration limit (Expiration Limit) on the weight of the sorbent in the generator column: 1—the volume of 0.34 cm³ (weight 0.8 g; $C_{Ca}$=14.3 μmol/g; $C_{Sr}$=1.4 mmol/g); 2—the volume of 1.6 cm³ (weight 3.8 g; $C_{Ca}$=3.0 μmol/g; $C_{Sr}$=0.3 μmol/g); 3—the volume of 3.0 cm³ (weight 7.2 g; $C_{Ca}$=1.6 μmol/g; $C_{Sr}$=0.16 μmol/g); 4—volume 5.0 cm³ (weight 12 g; $C_{Ca}$=1.0 μmol/g; $C_{Sr}$=0.1 μmol/g). The amount of $Sr^{2+}$ in each column is 1.1 μmol; the amount of $Ca^{2+}$ in each column is 11 μmol. Internal diameter and height of the columns: 1-0.4 cm and 2.7 cm; 2-085 cm and 2.7 cm; 3-0.85 cm and 5.4 cm; 4-1.15 cm and 4.8 cm.
Figure 4:
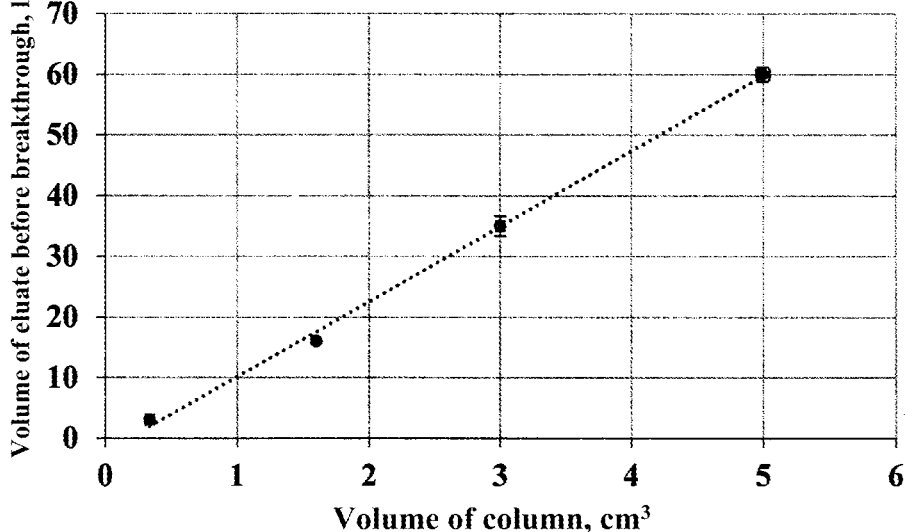
FIG. 4 shows the dependence of the total volume of eluate from the strontium-82/rubidium-82 generator before reaching the expiration limit (Expiration Limit) of strontium-82 on the volume of the generator column: 1—the volume of 0.34 cm³ (weight 0.8 g; $C_{Ca}$=14.3 μmol/g; $C_{Sr}$=1.4 mmol/g); 2—the volume of 1.6 cm³ (weight 3.8 g; $C_{Ca}$=3.0 μmol/g; $C_{Sr}$=0.3 μmol/g); 3—the volume of 3.0 cm³ (weight 7.2 g; $C_{Ca}$=1.6 μmol/g; $C_{Sr}$=0.16 μmol/g); 4—volume 5.0 cm³ (weight 12 g; $C_{Ca}$=1.0 μmol/g; $C_{Sr}$=0.1 μmol/g). Internal diameter and height of the columns: 1-0.4 cm and 2.7 cm; 2-085 cm and 2.7 cm; 3-0.85 cm and 5.4 cm; 4-1.15 cm and 4.8 cm.
Figure 5:
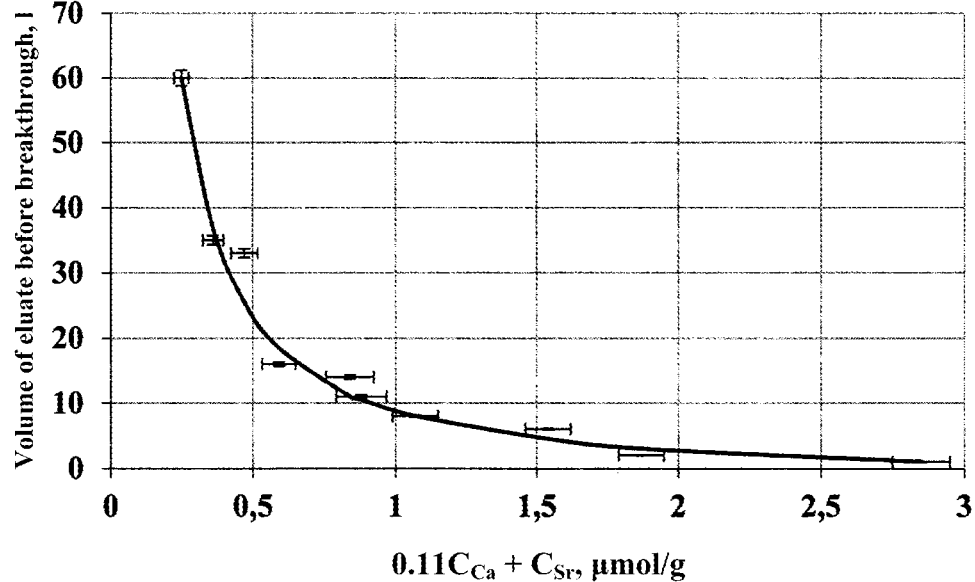
FIG. 5 shows the dependence of the total volume of eluate before reaching the expiration limit (Expiration Limit) on the total content of inactive strontium and calcium cations on the sorbent in the generator column in the ratio of 0.11 $C_{Ca}$+$C_{Sr}$ (μmol/g of the sorbent) for a standard column with a volume of 1.6 cm³ with a dry sorbent weight of 3.8 g.

Table. 2, FIGS. 3 and 4 illustrate the dependence between the total volume of eluate from the strontium-82/rubidium-82 generator before the strontium radionuclides breakthrough and the weight of the sorbent in the generator column and the volume of the generator column (hermetically sealed cylindrical container tube). This example shows that the total volume of eluate from the generator increases linearly with the weight of the sorbent or the generator column volume.

Table 2. The volume of the passed isotonic solution of 0.9% NaCl (V) before the content of the Alert Limit (0.002 kBq$^{82}$Sr/MBq $^{82}$Rb) and the Expiration Limit (0.01 kBq$^{82}$Sr/MBq $^{82}$Rb) of the strontium-82 breakthrough in the eluate from the strontium-82/rubidium-82 generators with different volume of generator columns and the weight of the sorbent in them is reached.

| Volume of column, cm³ | Dry sorbent weight, g | Content of inactive cations on the sorbent, μmol/g | | The volume of the passed isotonic solution before the strontium 82 breakthrough, I | |
|---|---|---|---|---|---|
| | | $C_{Ca}$ | $C_{Sr}$ | Up to the Alert Limit | Up to the Expiration Limit |
| 0.34 | 0.8 | 14.3 | 1.43 | 2 | 3 |
| 1.6 | 3.8 | 30 | 0.30 | 14 | 16 |
| 3.0 | 7.2 | 1.6 | 0.16 | 32 | 35 |
| 5.0 | 12.0 | 1.0 | 0.10 | 57 | 60 |

Thus, this technical solution makes it possible to obtain an radiopharmaceutical solution with a volume of more than 30 liters by controlling the content of the main inactive impurities of strontium and calcium cations in the strontium-82 chloride solution used when loading the generator. This significantly increases the yield of the generator and reduces the risk of strontium isotope breakthrough during long-term operation of the generator (with large volumes of radiopharmaceutical solution), i.e. reduces the risk of radioactive strontium entering the patient's body.

The invention claimed is:

1. A process for preparing a strontium-82/rubidium-82 generator, comprising the steps of:

filling a column volume with a sorbent made of hydrated tin (IV) oxide, passing through the column an initial solution with strontium-82 radionuclide, which also contains ions of stable isotopes of calcium and strontium, washing out rubidium-82 with a saline solution of 0.9% sodium chloride, wherein to achieve a breakthrough of strontium-82 or strontium-85 below permissible levels (0.01 and 0.1 kBq per 1 MBq $^{82}$Rb, respectively) when passing not less than 17 liters of saline solution through columns with a volume of not less than 1.6 cm³ and a dry sorbent weight of not less than 3.8 g, a specific activity of strontium-82 in the initial solution is not less than 90 GBq (2400 mCi) per mg of stable strontium cations for a generator with an activity of 3700 MBq (100 mCi).

2. The process as claimed in claim 1, wherein in order to achieve a breakthrough of strontium-82 or strontium-85 not more than 0.01 kBq and 0.1 kBq per 1 MBq $^{82}$Rb, respectively, when passing not less than 30 liters of saline solution through columns with a volume of not less than 1.6 cm³, and a dry sorbent weight of not less than 3.8 g, a specific activity of strontium-82 in the initial solution is not less than 180 GBq (4800 mCi) per mg of stable strontium cations for a generator with an activity of 3700 MBq (100 mCi).

3. The process as claimed in claim 1, wherein in order to achieve a breakthrough of strontium-82 or strontium-85 not more than 0.01 kBq and 0.1 kBq per 1 MBq $^{82}$Rb, respectively, when passing not less than 60 liters of saline solution through columns with a volume of not less than 1.6 cm³, and a dry sorbent weight of not less than 3.8 g, a specific activity of strontium-82 in the initial solution is not less than 290 GBq (7900 mCi) per mg of stable strontium cations for a generator with an activity of 3700 MBq (100 mCi).

4. A process for preparing a strontium-82/rubidium-82 generator, comprising the steps of:

filling a column volume with a sorbent of hydrated tin (IV) oxide, passing through the column an initial solution with strontium-82 radionuclide, which also contains ions of stable isotopes of calcium and strontium, and washing out rubidium-82 with a saline solution of 0.9% sodium chloride, wherein to achieve a breakthrough of strontium-82 or strontium-85 below permissible levels (0.01 and 0.1 kBq 1 MBq $^{82}$Rb, respectively) when passing not less than 17 liters of saline solution, a content of stable isotopes of strontium and calcium in a solution containing strontium-82 radionuclide passed through the column during loading the generator is chosen such that it (1 μmol of strontium cations+0.11 μmol of calcium cations) does not exceed 0.67 μmol per 1 g of dry sorbent in columns with a volume of 1.6 cm³ to 3.0 cm³ and a dry sorbent weight of 3.8 g to 7.2 g of dry sorbent.

5. The process as claimed in claim 4, wherein in order to achieve a breakthrough of strontium-82 or strontium-85 below permissible levels (0.01 and 0.1 kBq per 1 MBq $^{82}$Rb, respectively) when passing not less than 30 liters of saline solution, a content of ions of stable isotopes of strontium and calcium in the solution passed through the column during loading the generator, containing strontium-82 radionuclide, is chosen such that it (1 μmol of strontium ions+0.11 μmol of calcium cations) does not exceed 0.33 μmol per 1 g of dry sorbent.

6. The process as claimed in claim 4, wherein to achieve a breakthrough of strontium-82 or strontium-85 below permissible levels (0.01 and 0.1 kBq per 1 MBq $^{82}$Rb, respectively) when passing not less than 60 liters of saline solution, a content of ions of stable isotopes of strontium and calcium in the solution passed through the column during loading the generator, containing strontium-82 radionuclide, is chosen such that it (1 μmol of strontium ions+0.11 μmol of calcium cations) does not exceed 0.22 μmol per 1 g of dry sorbent.

* * * * *